United States Patent
Joshi et al.

(10) Patent No.: US 6,320,079 B1
(45) Date of Patent: Nov. 20, 2001

(54) PROCESS FOR THE PREPARATION OF S(ω-AMINOALKYLAMINO) ALKYL ARYL SULFIDE DIHYDROCHLORIDES

(75) Inventors: Uma Joshi; Syed Kalbey Raza; Pravin Kumar; Rajagopalan Vijayaraghavan; Devendra Kumar Jaiswal, all of Gwalior (IN)

(73) Assignee: The Chief Controller, Research & Ministry of Defense, Goverment of India, New Delhi (IN)

( * ) Notice: Subject to any disclaimer, the term of this patent is extended or adjusted under 35 U.S.C. 154(b) by 0 days.

(21) Appl. No.: 09/533,728

(22) Filed: Mar. 23, 2000

(30) Foreign Application Priority Data

Apr. 8, 1999 (IN) .............................. 0547/DEL/99

(51) Int. Cl.$^7$ ................................. C07C 321/16
(52) U.S. Cl. .............................................. 564/440
(58) Field of Search .................... 564/428, 440; 568/38

(56) References Cited

PUBLICATIONS

CA:107:88361 abs of Zh. Obshch. Khim. by Ukraintsev et al 56(8) pp 1856–8, 1986.*
CA:99:104882 abs of Pol J Chem by Bal et al 55(10) p 2171–5, 1981.*
CA: 109:54401 abs of Pol J Chem by Majewski et al 61(4–6) pp 557–61, 1987.*

* cited by examiner

Primary Examiner—Jean F. Vollano
(74) Attorney, Agent, or Firm—Venable; George H. Spencer; Ashley J. Wells

(57) ABSTRACT

A process for preparing S-(ω-aminoalkylamino) alkyl aryl sulfide dihydrochlorides includes the steps of (a) reacting aryl mercaptan and (ω-aminoalkylamino) alkylbromide dihydrobromide to cause condensation thereof in the presence of an organic base in an organic solvent and provide a condensation product; (b) converting the condensation product to a dihydrochloride salt; and (c) precipitating the dihydrochloride salt. Preferably the precipitated dihydrochloride salt is recrystallized. These dihydrochlorides are new and effective antidotes for sulfur mustard toxicity.

14 Claims, No Drawings

PROCESS FOR THE PREPARATION OF S(ω-AMINOALKYLAMINO) ALKYL ARYL SULFIDE DIHYDROCHLORIDES

FIELD OF INVENTION

This invention relates to a process for preparation of S-(ω-aminoalkylamino) alkyl aryl sulfide dihydrochlorides particularly S-2 (2-aminoethylamino) ethyl phenyl sulfide dihydrochloride, and to a process for the preparation thereof. Without implying any limitation on the scope of invention, the compound of the present invention has application as a new and effective antidote against highly toxic sulfur mustard (SM).

PRIOR ART

Sulfur mustard (SM) is a highly toxic chemical and a well known chemical warfare agent. This chemical attacks not only skin but all epithelial tissues with which it comes into contact including those of eyes and airways. Exposure to higher doses of sulfur mustard causes systemic toxicity with little or no involvement of the eyes, respiratory tract or skin. The signs and symptoms of systemic poisoning are similar to those caused by nuclear radiation.

One type of antidote known in the art is a SM scavenger, which is comprised of compounds that prevent alkylation of critical targets. Representative members of this class that have been tested are sodium thiosulfate, N-acetyl-L-cysteine, and several other sulfur compounds such as thiophosphonates, thiophosphates and thiocarbamates. These classes of compounds have several disadvantages that would preclude their practical use as antidotes for the systemic toxicity of sulfur mustard. One such disadvantage is that such compounds can only be administered intravenously thereby making them unsuitable for self-administration. Another disadvantage is that such compounds are suitable only for pretreatment. A further disadvantage for use as antidotes against SM is that these compounds are excreted rapidly by the kidney after which their efficacy as an SM scavenger is lost.

Another type of compound known in the art is a NAD level stabilizer. Nicotinamide and nicotinic acids have been tested as representatives of this class. Although some of these compounds under certain circumstances have been found effective in preventing SM toxicity, these also suffer from certain drawbacks. One such drawback is that they are effective in lymphocytes but not in cultured keratinocytes. Another disadvantage is that, if these compounds are administered 24 hours after SM exposure, they fail to provide any protection against SM toxicity. Still another disadvantage is that these compounds fail to prevent SM-induced adenosine triphosphate (ATP) loss in the cells and thus these compounds provide only short term cytoprotection. A further disadvantage is that these compounds can only be administered parenterally.

OBJECTS OF PRESENT INVENTION

A primary object of this invention is to propose S-(ω-aminoalkylanino) alkyl aryl sulfide dihydrochlorides, particularly S-2(2-aminoethylamino) ethyl phenyl sulfide dihydrochloride, and a process for the preparation thereof for use as a new and effective antidote against sulfur mustard, which is a highly toxic and known chemical warfare agent.

Another object of this invention is to propose a process which provides S-(ω-aminoalkylamino) alkyl aryl sulfide dihydrochlorides, particularly S-2(2-aminoethylamino) ethyl phenyl sulfide dihydrochloride, which can be administered both orally as well as parenterally as an antidote against sulfur mustard, thereby making the compound suitable for self-administration.

Still another object of this invention is to propose a process for preparation of S-(ω-aminoalkylamino) alkyl aryl sulfide dihydrochlorides particularly S-2(2-aminoethylamino) ethyl phenyl sulfide dihydrochloride which is effective antidote as a pretreatment and also as a therapeutic agent.

A further object of the present invention is to propose a process for preparation of S-(ω-aminoalkylamino) alkyl aryl sulfide dihydrochlorides, particularly S-2(2-aminoethylamino) ethyl phenyl sulfide dihydrochloride, which provides cytoprotection.

DESCRIPTION OF THE INVENTION

According to this invention there is provided S-(ω-aminoalkylamino) alkyl aryl sulfide dihydrochlorides.

In accordance with the present invention, a process is provided for the preparation of S-(ω-aminoalkylamino) alkyl aryl sulfide dihydrochlorides, particularly S-2(2-aminoethylamino) ethyl phenyl sulfide dihydrochloride, which is a new and effective antidote against sulphur mustard, which is a known chemical warfare agent. The process comprises condensation of S-(ω-aminoalkylamino) alkyl aryl sulfide dihydrochlorides with aryl mercaptans in the presence of an organic base in an organic solvent. The organic base used is primary or secondary or tertiary alkylamine or arylamine. Particularly for preparation of S-2(2-aminoethylamino) ethyl phenyl sulfide dihydrochloride, the organic base preferably used is triethylamine. The organic solvents used are chloroform or carbon tetrachloride or dimethyl sulfoxide or dimethyl formamide. Particularly for preparation of S-2(2-aminoethylamino) ethyl phenyl sulfide dihydrochloride, the organic solvent preferably used is chloroform. The reaction is carried out at −15 to +15° C. with efficient stirring for 2–5 hours. The residue comprising the free base is converted to its dihydrochloride salt by treatment with concentrated hydrochloric acid. The antidote against SM, prepared by the process of the present invention, can be administered both orally as well as intraperitoneally making it a unique compound which is suitable for self-administration. The compound is effective as a pretreatment as well as a therapeutic agent and provides cytoprotection in cases of systemic toxicity. The process provides 60–65% yield of compound with a very high purity of more than 99%.

Specifically, the process comprises preparation of a suspension of a mixture of (ω-aminoalkylamino) alkylbromide dihydrobromide and aryl mercaptan taken in 1:1.2 molar ratio in an appropriate quantity of an organic solvent. Specifically for preparation of S-2(2-aminoethylaimino) ethyl phenyl sulfide dihydrochloride, (2-aminoethylamino) ethylbromide dihydrobromide and thiophenol are taken in the above molar ratio. The organic solvent taken is either dry chloroform or carbon tetrachloride or dimethyl sulfoxide or dimethyl formamide preferably dry chloroform.

The suspension is cooled to a temperature of −15 to +15° C., preferably at 0–5° C. and an organic base added with is either primary or secondary or tertiary alkylamine or arylarnine, preferably a tertiary alkylamine or arylamine. Specifically, for preparation of S-2(2-aminoethylamino) ethyl phenyl sulfide dihydrochloride, the organic base preferably taken is triethylamine which is taken in a quantity four times the quantity of bromide salt, with constant stirring, over a period of around 1 hour. Stirring is continued preferably at 0–5° C. for 3–5 hours followed by further stirring at 20 to 40° C. for 3–5 hours and then left at the same temperature for overnight.

The next steps comprises washing with water to remove the triethylamine salt, making the aqueous layer alkaline with sodium hydroxide, and extracting twice with chloroform.

The combined chloroform extracts are dried over anhydrous sodium sulfate and evaporated under reduced pressure. The residue is diluted with a mixture of benzene and ethanol taken in 1:1 ratio, and the solvent is removed repeatedly in order to remove traces of triethylamine and moisture.

The residue is dissolved in ethanol and concentrated hydrochloric acid is added until the solution becomes acidic.

The white dihydrochloride salt of the product is precipitated by addition of sufficient quantity of acetone until the completion of precipitation. The contents are kept under refrigeration for 2 hours, filtered and dried at room temperature.

The dried solid is boiled with chloroform for 10 to 30 minutes to remove any triethylamine hydrochloride salt, followed by filtering while hot and drying at room temperature.

The solid obtained by boiling is dissolved in methanol, just sufficient to dissolve the solid, followed by treatment with activated charcoal and addition of acetone until the crystallization, i.e., recrystallization, is complete. Thereafter, the white crystalline solid is filtered out and dried at room temperature to get a final product with a very purity of more than 99% and yield of 60–65%.

The process of the present invention will now be illustrated with a working example which is intended to be illustrative example particularly for preparation of S-2(2-aminoethylamino) ethyl phenyl sulfide dihydrochloride and is not intended to be taken restrictively to imply any limitation on the scope of the present invention.

EXAMPLE

A two necked round bottom flask equipped with a guard tube and pressure equilibrating funnel was charged with dry chloroform (500 ml) and was cooled to 0–5° C. Thiophenol (0.3 mol) and (2-aminoethylamino) ethyl-bromide dihydrobromide (0.25 mol) were added to the well stirred chloroform. Triethylamine (1 mol) was added dropwise to the above solution over a period of one hour. The reaction mixture was stirred first at 0–5° C. for three hours and then at room temperature for an additional three hours and then left as such overnight. The contents were washed with water (200 ml) and extracted with chloroform (600 ml). After a first extraction, sodium hydroxide (0.5 mol) was added to the aqueous layer and it was extracted twice with chloroform (200 ml each). The chloroform extracts were combined, dried over anhydrous sodium sulfate and evaporated under reduced pressure. Benzene (50 ml) and ethanol (50 ml) were added to the residue and removed repeatedly in order to remove any triethylamine and moisture. The contents were diluted with ethanol (100 ml) and concentrated hydrochloric acid was added dropwise till the mixture was acidic to the pH paper. Acetone in sufficient quantity was then added to precipitate the white dihydrochloride salt of the desired product. The which solid, after keeping under refrigeration for two hours, was filtered, dried and then boiled for 10 minutes with chloroform (500 ml) and filtered hot. The solid thus obtained was dissolved in a minimum amount of methanol and treated with activated animal charcoal. From the filtrate, the compound was obtained by adding sufficient acetone to cause crystallization/precipitation. White crystalline solid thus obtained was filtered and dried to get S-2(2-aminoethylamino) ethyl phenyl sulfide dihydrochloride in pure form.

The compound obtained by the process of the present invention and illustrated in this example has the following properties:

| PROPERTIES | |
| --- | --- |
| Melting Point | 194–195° C. |
| Thin Layer Chromatography | More than 99% Pure [Methanol:Chloroform:Ammonia (1:3:1)] |
| Spectral Data | IR(KBr, cm$^{-1}$): 1611, 1530, 1438, 737 |
| HNMR(CDOD): 3.38(8H, m); | 7.44(5H, m) + MS(ESI): m/z 197 (M + H) |
| Stability | Stable in both Acidic and Basic Media. |

PHARMACOLOGICAL EVALUATION OF THE COMPOUND

The pharmacological evaluation, particularly of S-2(2-aminoethylamino) ethyl phenyl sulfide dihydrochloride has been carried out on randomly bred adult female Swiss mice weighing 25–28 gm each. For the estimation of $LD_{50}$ of the compounds, freshly prepared solutions of the compounds were administered intraperitonially or orally. The compounds were administered as a single injection or as a single feeding and the animals were observed for mortality for a period of fourteen days.

For the protection studies, sulphur mustard was applied topically on the back of mice after closely clipping the hair. Freshly prepared solutions of the compound in distilled water were injected or given orally and the animals were observed for mortality for fourteen days. The results were analyzed statistically and it was found that S-2(2-aminoethylamino) ethyl-phenyl sulfide dihydrochloride provided significant protection both parenterally as well as orally.

It is to be understood that the process of the present invention is susceptible to modifications, adaptations and changes by those skilled in the field of art. Such modifications, adaptations and changes are intended to be within the scope of the present invention which is set forth in the claims.

What is claimed is:

1. A process for preparing S-(ω-aminoalkylamino) alkyl aryl sulfide dihydrochlorides, comprising the steps of:
   a. reacting aryl mercaptan and (ω-aminoalkylamino) alkylbromide dihydrobromide to cause condensation thereof in the presence of an organic base in an organic solvent and provide a condensation product;
   b. converting the condensation product to a dihydrochloride salt; and
   c. precipitating the dihydrochloride salt.

2. The process according to claim 1, wherein the aryl mercaptan is thiophenol.

3. The process according to claim 1, wherein the (ω-aminoalkylamino) alkylbromide dihydrobromide is (2-aminoethylamino) ethylbromide dihydrobromide.

4. The process according to claim 1, wherein the organic base is selected from the group consisting of primary alkylamine, secondary alkylamine, tertiary alkylamine, primary arylamine, secondary arylamine, and tertiary arylamine, and wherein the organic solvent is selected from the group consisting of dry chloroform, carbon tetrachloride, dimethyl sulfoxide, and dimethyl formamide.

5. The process according to claim 4, wherein the organic base is tertiary alkylamine, and wherein the organic solvent is dry chloroform.

6. The process according to claim 1, wherein reacting is carried out a temperature ranging from −15 to +15° C.

7. The process according to claim 6, wherein reacting is carried out a temperature ranging from 0 to 5° C.

8. The process according to claim 1, wherein converting the condensation product to a dihydrochloride salt is carried out by adding concentrated hydrochloric acid to the condensation product.

9. The process according to claim 1, wherein precipitating the dihydrochloride salt is carried out by adding acetone to the dihydrochloride salt.

10. The process according to claim 1, further comprising recrystallizing the dihydrochloride salt.

11. The process according to claim 10, wherein recrystallizing the dihydrochloride salt includes dissolving the precipitated dihydrochloride salt in an organic solvent.

12. The process according to claim 11, wherein the organic solvent is methanol.

13. The process according to claim 11, wherein recrystallizing the dihydrochloride salt further includes adding acetone to the dissolved dihydrochloride salt to precipitate the dihydrochloride salt.

14. The process according to claim 1, further comprising the step of providing (ω-aminoalkylamino) alkylbromide dihydrobromide and aryl mercaptan in a molar ratio of 1:1.2 prior to reacting.

* * * * *